(12) United States Patent
Leiske et al.

(10) Patent No.: US 11,806,355 B2
(45) Date of Patent: Nov. 7, 2023

(54) ORGANIC POLYMER PARTICLES CONTAINING POLY(OXAZOLINE) STABILIZERS AND USE OF POLY(OXAZOLINES) FOR STABILIZING ORGANIC POLYMER PARTICLES

(71) Applicant: Friedrich-Schiller-Universitaet Jena, Jena (DE)

(72) Inventors: Meike Nicole Leiske, Jena (DE); Anja Traeger, Trebgast (DE); Ulrich Sigmar Schubert, Jena (DE)

(73) Assignee: Friedrich-Schiller-Universitaet Jena, Jena (DE)

( * ) Notice: Subject to any disclaimer, the term of this patent is extended or adjusted under 35 U.S.C. 154(b) by 0 days.

(21) Appl. No.: 16/493,368

(22) PCT Filed: Mar. 12, 2018

(86) PCT No.: PCT/EP2018/000094
§ 371 (c)(1),
(2) Date: Dec. 19, 2019

(87) PCT Pub. No.: WO2018/166651
PCT Pub. Date: Sep. 20, 2018

(65) Prior Publication Data
US 2020/0122106 A1   Apr. 23, 2020

(30) Foreign Application Priority Data
Mar. 14, 2017 (DE) .......................... 102017002454.5

(51) Int. Cl.
*A61K 9/00* (2006.01)
*A61K 31/553* (2006.01)
(Continued)

(52) U.S. Cl.
CPC .......... *A61K 31/553* (2013.01); *A61K 9/1647* (2013.01); *C08L 67/04* (2013.01);
(Continued)

(58) Field of Classification Search
CPC ...................................................... C09K 23/16
See application file for complete search history.

(56) References Cited

U.S. PATENT DOCUMENTS

| 5,837,768 A | 11/1998 | Warchol |
| 2008/0131395 A1 | 6/2008 | Wellinghoff |

(Continued)

FOREIGN PATENT DOCUMENTS

| CN | 102552146 B | 8/2013 |
| EP | 0152551 A1 | 8/1985 |

(Continued)

OTHER PUBLICATIONS

Wang, Polymeric micelles with a pH-responsive structure as intracellular drug carriers, Journal of Controlled Release, 2005, 108, 140-149.*

(Continued)

*Primary Examiner* — Paul W Dickinson
(74) *Attorney, Agent, or Firm* — Abel Schillinger, LLP

(57) ABSTRACT

The invention relates to compositions containing water-soluble poly(oxazoline) and organic polymer particles chosen from the group of polyolefins, polyvinyl aromatics, polyvinyl esters, polyesters, polyamides, polyimides, polycarboxylic acids, polycarboxilic acid esters, polycarboxylic acid amides, polynitriles, polysulfonic acids, polyketones, polysulfones, polymeric polyols, polyurethanes, proteins, polymeric carbohydrates, nucleic acids or from a mixture of two or more of these polymers. The water-soluble poly (oxazolin) acts as a stabilizer for the polymer particles and (Continued)

$^1$H-NMR (300 MHz, CDCl$_3$) of P(EtOx)$_{61}$ can particularly advantageously be used as a stabilizer in the freeze-drying of aqueous polymer dispersions.

18 Claims, 1 Drawing Sheet

(51) Int. Cl.
| | | |
|---|---|---|
| C09D 7/65 | (2018.01) | |
| C09D 7/45 | (2018.01) | |
| A61K 9/16 | (2006.01) | |
| C08L 67/04 | (2006.01) | |
| C09D 133/06 | (2006.01) | |
| C09D 167/04 | (2006.01) | |
| C09K 23/16 | (2022.01) | |

(52) U.S. Cl.
CPC ............... C09D 7/45 (2018.01); C09D 7/65 (2018.01); C09D 133/062 (2013.01); C09D 167/04 (2013.01); C09K 23/16 (2022.01)

(56) References Cited

U.S. PATENT DOCUMENTS

| | | | |
|---|---|---|---|
| 2010/0041592 A1* | 2/2010 | Kabanov | A61K 47/32 514/1.1 |
| 2014/0158931 A1 | 6/2014 | Poncelet | |
| 2017/0157147 A1* | 6/2017 | Hanes | A61K 31/573 |

FOREIGN PATENT DOCUMENTS

| | | |
|---|---|---|
| EP | 0419793 A1 | 4/1991 |
| WO | 2006112538 A1 | 10/2006 |
| WO | 2012094620 A1 | 7/2012 |
| WO | 2016087598 A1 | 6/2016 |
| WO | 201528685 A1 | 3/2019 |

OTHER PUBLICATIONS

Koshkina, Tuning the Surface of Nanoparticles: Impact of Poly(2-ethyl-2-oxazoline) on Protein Adsorption in Serum and Cellular Uptake, Macromolecular Bioscience, 2016, 16, 1287-1300.*
J. Food Sci. 2011, 76, 16-24, Gomes, C., Moreira, RG, Castell-Perez, E. Poly(DL-lactide-co-glycolide) (PLGA) nanoparticles with entrapped trans-cinnamaldehyde and eugenol for antimicrobial delivery applications.
Int. J. Pharm. 1999, 187, 143-152, Murakami, H., Kobayashi, M., Takeuchi, H. Kawashima, Y. Preparation of poly(DL-lactide-co-glycolide) nanoparticles by modified spontaneous emulsification solvent diffusion method).
React. Func. Polym. 2009, 69, 643-649, Giardi, C., Lapinte, V., Charnay, C., Robin, J. Nonionic poly(oxazoline) surfactants based on renewable source: Synthesis, surface and bulk properties).
Polymer J., 1992, 24, 405-409, Miyamoto, M., Aoi, K., Yamanaka, H., Saegusa, T. Preparation of block copolymer consisting of poly(2-methyl-2-oxazolines) and poly(propylene oxide) blocks. A new nonionic surfactant).
Macromolecules 1991, 24, 5473-5475, Kobayashi, S., Uyama, H. Synthesis of a nonionic polymeric surfactant from 2-oxazoline having a carboxylate component as the hydrophobic group).
Phosphorus Research Bulletin 2011, 25, 33-38. Amjad, Z .; Morgan, D. Efficacy of hydroxyapatite dispersants in the presence of surfactants.).
Nat. Commun. 2014, (5), 5565-5578. Press, A.T., Traeger, A., Pietsch, C., Mosig, A., Wagner, M., Clemens, M.G., Jbeily, N., Koch, N., Gottschaldt, M., Bézière, N., Ermolayev, V., Ntziachristos, V., Popp, J., Kessels, M.M., Qualmann, B., Schubert, US, Bauer, M. Cell type-specific delivery of short interfering RNAs by dye-functionalized theranostic nanoparticles).
Biomacromolecules, 2014, 15, 3753-3765, Fonte, P., Soared, S., Sousa, F., Costa, A. Seabra, V., Rice, S., Sarmento, B. Stability study perspective of the effect of freeze-drying using cryoprotectants on the structure of insulin loaded into PLGA nanoparticles).
Adv. Func. Mater. 2013, 24, 1133-1139. Kedracki, D .; Maroni, P.; Schlaad, H. Vebert-Nardin, C. Polymer-aptamer hybrid emulsion templating yields bioresponsive nanocapsules).
Wiesbrock, F. et al., Macromolecular Rapid Communications 2004, 25, 1895-1899.
International Search Report dated Jun. 7, 2018 with regard to International Application No. PCT/EP2018/000094.
International Preliminary Report on Patentability with regard to International Application PCT/EP2018/000094, dated Sep. 26, 2019 (with English Translation).

* cited by examiner

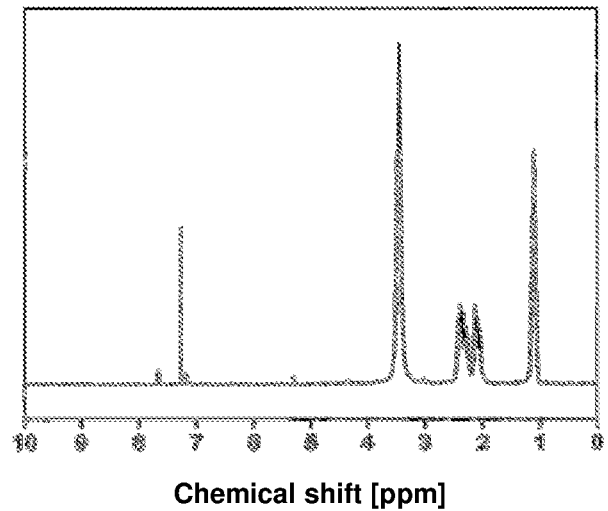
Figure 1: $^1$H-NMR (300 MHz, CDCl$_3$) of P(EtOx)$_{61}$
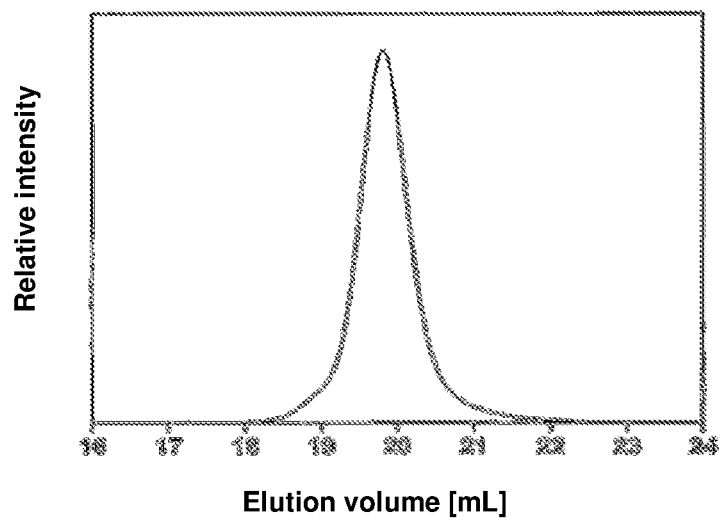
Figure 2: SEC elugram (DMAc + 0.21% LiCl, PS standard) of P(EtOx)$_{61}$

ORGANIC POLYMER PARTICLES CONTAINING POLY(OXAZOLINE) STABILIZERS AND USE OF POLY(OXAZOLINES) FOR STABILIZING ORGANIC POLYMER PARTICLES

The invention relates to the field of preparation and processing of polymer dispersions, preferably of polymer dispersions of nanoparticulate particles, and to polymer powders obtained by processing of polymer dispersions. In particular, the invention relates to the preparation and processing of poly(oxazoline)-stabilized organic polymer particles which are preferably contained in liquid water or in water-miscible liquids or which have been obtained by liquid removal from these liquids. This can preferably be done by freeze-drying (lyophilization).

It is known to stabilize polymer dispersions using surface active agents, such as tensides or protective colloids. Polymer dispersions can be produced directly from the monomers by selected polymerization techniques, such as emulsion or suspension polymerization, or by dispersing a polymer in a dispersant, such as water and/or a water-miscible liquid. To prepare these so-called secondary dispersions, polymer particles are obtained in a dispersing medium. This can be carried out, for example, by precipitating a polymer solution by addition of water or by the progressive dispersion of water in a polymer with the occurrence of a phase inversion or by dispersing a dissolved polymer by energy input, for example, by sonication.

It is known from the prior art that various auxiliaries can be used in the preparation of polymer particles for their stabilization. The stabilization of these polymer particles can be divided into the following areas:
  i) Stabilization of the polymer particles during the preparation and purification of polymer dispersions (stabilizing auxiliaries frequently referred to as "surfactants" or "tensides"),
  ii) Stabilization of polymer particles during the lyophilization and storage of polymer dispersions (stabilizing auxiliaries often referred to as "cryoprotectants") and
  iii) Stabilization of polymer particles during use in the dispersing medium, e.g., an aqueous system.

With regard to the stabilization of polymer particles during the preparation and purification of polymer dispersions, the following publications are to be mentioned:

C. Gomes et al. and H. Murakami et al. used poly(vinyl alcohol) (PVA) to stabilize poly(DL-lactide-co-glycolide) (PLGA) nanoparticles. The stabilization of the particles during production is therefore already known, but no poly(oxazoline)s are used for stabilization. PVA also has hemolytic properties, and its level must be greatly reduced prior to biological application (*J. Food Sci.* 2011, 76, 16-24, Gomes, C., Moreira, R G, Castell-Perez, E. Poly(DL-lactide-co-glycolide) (PLGA) nanoparticles with entrapped trans-cinnamaldehyde and eugenol for antimicrobial delivery applications and *Int. J. Pharm.* 1999, 187, 143-152, Murakami, H., Kobayashi, M., Takeuchi, H. Kawashima, Y. Preparation of poly(DL-lactide-co-glycolide) nanoparticles by modified spontaneous emulsification solvent diffusion method).

In WO 2015/28685 A1, poly(2-ethyl-2-oxazoline)s are used as a stabilizer for indomethacin during the precipitation of this substance, without using polymer particles. The benefit of the poly(oxazoline) is to ensure that the resulting indomethacin particles have a size <500 nm and improved solubility in water or medium, and that these particles can be redispersed. A stabilization of polymer particles by poly(oxazoline)s is not described.

C. Giardi et al. use lipid-poly(oxazoline) copolymers to form micelles. First a lipid macroinititator was prepared, with which the cationic ring-opening polymerization of 2-methyl-2-oxazoline was carried out. A series of different copolymers was prepared in which the chain length of the poly(2-oxazoline)s was varied. The synthesized copolymers were then tested for surface stabilization of the resulting micelles. The copolymers produced have been proposed for use as polymeric surfactants. Here, instead an amphiphilic block copolymer was used with a water-insoluble block (lipid). Stabilization of polymer particles by poly(oxazoline)s is not described (*React. Func. Polym.* 2009, 69, 643-649, Giardi, C., Lapinte, V., Charnay, C., Robin, J. Nonionic poly(oxazoline) surfactants based on renewable source: Synthesis, surface and bulk properties).

M. Miyamoto et al. prepared block copolymers consisting of poly(2-methyl-2-oxazoline) and poly(propylene oxide) to test their suitability as possible nonionic surfactants. The surface tension of the polymers was measured and compared with Pluronic® F68. The measured surface activity of the copolymers decreased with increasing hydrophilic polymer content. Stabilization of polymer particles by poly(oxazoline)s is not described (*Polymer J.*, 1992, 24, 405-409, Miyamoto, M., Aoi, K., Yamanaka, H., Saegusa, T. Preparation of block copolymer consisting of poly(2-methyl-2-oxazolines) and poly(propylene oxide) blocks. A new nonionic surfactant). From this document, the skilled person would deduce that hydrophilic poly(oxazoline)s are actually not suitable as surfactants.

S. Kobayashi and H. Uyama used copolymers consisting of a hydrophobic (fatty acid) and a hydrophilic (poly(2-ethyl-2-oxazoline) or poly(2-methyl-2-oxazoline)) segment to produce nonionic surfactants. To determine the surfactant properties, measurements of surface tension were made. Here instead an amphiphilic block copolymer with a water-insoluble fatty acid block was used. Stabilization of finely divided polymers by poly(oxazoline)s is not described (*Macromolecules* 1991, 24, 5473-5475, Kobayashi, S., Uyama, H. Synthesis of a nonionic polymeric surfactant from 2-oxazoline having a carboxylate component as the hydrophobic group).

Z. Amjad & D. Morgan used poly(2-ethyl-2-oxazoline) as a surfactant to stabilize hydroxyapatite in aqueous solution. Stabilization of polymer particles is not disclosed (*Phosphorus Research Bulletin* 2011, 25, 33-38. Amzad, Z.; Morgan, D. Efficacy of hydroxyapatite dispersants in the presence of surfactants.)

With regard to the stabilization of polymer particles during the lyophilization and storage of polymer dispersions, the following publications are to be mentioned:

US 2014/0158931 A1 describes poly(2-oxazoline) as a stabilizer for metal-based nanoparticles. The finished metal particles are suspended in aqueous solution and, in some cases, lyophilized. The poly(2-ethyl-2-oxazoline)s used have a described molar mass ($M_n$) of 50,000 g mol$^{-1}$. Stabilization of organic polymer particles is not disclosed.

CN 102552146 B describes the preparation and storage of liposomal doxorubicin and epirubicin. In this case, the liposomes are built up from phospholipids and contain surfactants or cryoprotectants. In this context, among other things, poly(2-ethyl-2-oxazoline) with a total content of up to 60% is given as the cryoprotectant. Stabilization of organic polymer particles is not disclosed.

A. T. Press et al. used polyvinyl alcohol for particle stabilization during lyophilization by previously adding 1 µg of the polymer to the particles. The stabilization of particles during lyophilization is therefore already known, but here polyvinyl alcohol is used as cryoprotectant (*Nat. Commun.* 2014, (5), 5565-5578. Press, A. T., Traeger, A., Pietsch, C., Mosig, A., Wagner, M., Clemens, M. G., Jbeily, N., Koch, N., Gottschaldt, M., Bézière, N., Ermolayev, V., Ntziachristos, V., Popp, J., Kessels, M. M., Qualmann, B., Schubert, U S, Bauer, M. Cell type-specific delivery of short interfering RNAs by dye-functionalized theranostic nanoparticles).

P. Fonte et al. used trehalose, glucose, sucrose, fructose or sorbitol at a concentration of 10 w/v % as an addition to the PLGA nanoparticles to lyophilize them. Accordingly, stabilization of the particles during lyophilization is already known, but carbohydrates selected as cryoprotectants are used (*Biomacromolecules,* 2014, 15, 3753-3765, Fonte, P., Soared, S., Sousa, F., Costa, A. Seabra, V., Rice, S., Sarmento, B. Stability study perspective of the effect of freeze-drying using cryoprotectants on the structure of insulin loaded into PLGA nanoparticles).

With regard to the stabilization of polymer particles during use in the dispersing medium, the following publications in the prior art are to be mentioned:

D. Kedracki et al. already used hydrophobic poly(2-oxazoline)s for covalent DNA binding. For this purpose, the original double bonds of the monomer units were partially reacted via a thiol-ene reaction to form amino groups. The resulting copolymers were used to directly bind DNA to the polymer and to provide surfactant character via the hydrophobic side chains of the copolymer. The use of water-soluble poly(oxazoline)s and stabilization of organic polymer particles is not disclosed (*Adv. Func. Mater.* 2013, 24, 1133-1139. Kedracki, D.; Maroni, P.; Schlaad, H. Vebert-Nardin, C. Polymer-aptamer hybrid emulsion templating yields bioresponsive nanocapsules).

WO 2016/087598 A1 discloses microcapsules with good storage stability. These consist of a core material and of an inner shell layer of polyvinyl alcohol and an outer shell layer of poly(oxazoline). Core materials are water-insoluble substances, including compounds known as polyesters. It is apparent from the description that it means esters of polycarboxylic acids with $C_4$-$C_{30}$ alcohols and no organic polymers. Thus, this document does not disclose a combination of organic polymer particles with poly(oxazoline)s.

The poly(oxazoline) surfactants described in the prior art consist largely of copolymers containing a hydrophilic moiety, namely the moiety derived from the polymerization of oxazoline, and a hydrophobic moiety, namely the moiety derived from the polymerization of hydrophobic monomers. By combining these structural units in one molecule, interactions both with the hydrophobic polymer particle and with the hydrophilic dispersion medium can be ensured. In addition, the poly(oxazoline) surfactants can form their own nano- or microstructures in an aqueous medium. A low-molecular-weight substance, in aqueous solution, poly(2-ethyl-2-oxazoline) homopolymer has hitherto been proposed as a stabilizer only for the production of indomethacin particles.

Polymer-based particle systems, e.g., PLGA, are usually stabilized by the addition of polyvinyl alcohol during preparation and purification. However, polyvinyl alcohol shows cytotoxicity and therefore leads to the need to subsequently purify prepared particles, for example by centrifugation.

The stabilization of organic polymer particles, such as polymer-based nanoparticles or microparticles, with the aid of water-soluble poly(oxazoline)s, such as poly(2-ethyl-2-oxazoline) or poly(2-methyl-2-oxazoline), as surfactants has not been described up to now. These poly(oxazoline)s are hydrophilic polymers.

Furthermore, the use of agents for surface stabilization and structure preservation after lyophilization (cryoprotectants) is basically known. Standard agents used are sugars (e.g., trehalose, glucose or sucrose), which are added in comparatively large amounts of about 5-10 v/w % before lyophilization. The use of these sugars leads to very good resuspension of the particles. However, uptake mechanisms of these particles can be influenced or altered by the interaction with sugar transporters (GLUT transporters) on the cell surfaces. In addition, sugars are hygroscopic and can lead to problems in the storage of the particles produced. Furthermore, sugars are osmotically active, which is often an undesirable factor for biological systems. The stabilization of organic polymer particles, in particular of nanoparticles, by means of polyvinyl alcohol during lyophilization is also possible. However, this can lead to increased cytotoxicity.

The stabilization of organic polymer particles, in particular of nano- or microparticles, with the aid of poly(oxazoline)s, such as poly(2-ethyl-2-oxazoline) or poly(2-methyl-2-oxazoline) as cryoprotectants, has not previously been described.

An object of the present invention is to provide organic polymer particles which may be dispersed in hydrophilic liquids and whose dispersions are distinguished by excellent stability.

Another object of the present invention is to provide organic polymer particles which may be in powder form and which are excellent in stability.

Another object of the present invention is to provide dispersions of organic polymer particles in hydrophilic liquids which can be purified and/or worked up readily and without significant particle size change, for example by freeze-drying or by centrifugation or by filtration.

Another object of the present invention is to provide cryoprotectants for organic polymer particles dispersed in hydrophilic liquids.

The present invention relates to compositions comprising water-soluble poly(oxazoline) and organic polymer particles selected from the group of polyolefins, polyvinylaromatics, polyvinyl esters, polyesters, polyamides, polyimides, polycarboxylic acids, polycarboxylic acid esters, polycarboxylic acid amides, polynitriles, polysulfonic acids, polyketones, polysulfones, polymeric polyols, polyurethanes, proteins, polymeric carbohydrates, nucleic acids or a mixture of two or more of these polymers.

As used herein, "hydrophilic liquids" means water and/or water-miscible liquids, such as alcohols of one to four carbon atoms or ketones of two to six carbon atoms.

For the purposes of the present description, "polymer particles" is to be understood as meaning particulate polymers of the abovementioned groups of substances. The particles may be dispersed in liquid form in a hydrophilic liquid or the particles are preferably in solid form, either dispersed in a hydrophilic liquid or in the form of a powder. The size of the particles can be determined by visual methods, for example by microscopy; for particle sizes in the nanoscale, light scattering or electron microscopy can be used. The shape of the polymer particles may be arbitrary, for example, spherical, ellipsoidal or irregular. The polymer particles can also form aggregates of several primary particles. Preferably, the particles of organic polymers are in the form of nanoparticles. In addition to the organic polymers, the particles may contain further constituents, for example active ingredients or auxiliaries or additives.

The terms "particulates" and "particles" are used synonymously in the context of the present description.

For the purposes of the present description, "nanoparticles" are particles whose diameter is less than 1 μm and which may be composed of one or more molecules. They are generally characterized by a very high surface-to-volume ratio and thus present very high chemical reactivity. Nanoparticles can consist of polymers or contain other constituents in addition to the polymers, such as active ingredients or auxiliaries or additives.

For the purposes of the present description, "polymers" are understood to mean the abovementioned organic compounds which are characterized by the repetition of specific units (monomer units or repeat units). Polymers may consist of one or more types different of repeat units. Polymers are produced by the chemical reaction of monomers to form covalent bonds (polymerization) and form the so-called polymer backbone by linking the polymerized units. These may have side chains on which functional groups may be located. If these polymers have hydrophobic properties to some extent, they can form nanoscale structures (e.g., nanoparticles, micelles, vesicles) in an aqueous environment. Homopolymers consist of only one monomer unit. On the other hand, copolymers consist of at least two different monomer units, which may be arranged in a statistical, gradient, alternating or block manner.

For the purposes of the present description, "cryoprotectants" are to be understood as meaning water-soluble substances or substance mixtures which serve to stabilize a particle during lyophilization (freeze-drying). They can be added to the particles dispersed in the dispersion medium, for example the particle suspension, during the preparation or afterwards (but before the lyophilization). Furthermore, these substances or mixtures are not covalently bound to the particle.

In the context of the present description, "surface-active agents" or "surfactants" are to be understood as meaning water-soluble substances or substance mixtures which serve to stabilize particles during production and storage in aqueous media. They are usually added to the dispersion medium, for example the aqueous phase, during the preparation of the particles, but can also be added after their preparation to stabilize the resulting dispersion.

In the context of the present description, "water-soluble compounds" or "water-soluble poly(oxazoline)s" are to be understood as meaning compounds or poly(oxazoline)s which dissolve up to at least 50 g/L of water at 25° C.

In the context of the present description, "active substances" are compounds or mixtures of compounds which have a desired effect on a living organism. These may be, for example, pharmaceutically active substances or agrochemically active substances. Active substances can be low- or high-molecular-weight organic compounds. The active substances are preferably low-molecular-weight pharmaceutically active substances or higher molecular weight pharmaceutically active substances; in particular, hydrophilic active substances from potentially therapeutically usable nucleic acids (e.g., short interfering RNA, short hairpin RNA, micro RNA, plasmid DNA) or from potentially usable proteins (e.g., antibodies, interferons, cytokines) can be used.

The term "pharmaceutically active substance" is understood to mean any inorganic or organic molecule, substance or compound that has a pharmacological effect. The term "pharmaceutically active substance" is used synonymously herein with the term "medicine".

In this case, active substances can be those which have little or no bioavailability without inclusion in a nanoparticle or a liposome, have little or no stability in vivo or should only act in specific cells of an organism.

For the purposes of the present description, "auxiliaries and additives" are to be understood as meaning substances which are added to a formulation in order to give it certain additional properties and/or to facilitate its processing. Examples of auxiliaries and additives are tracers, contrast agents, carriers, fillers, pigments, dyes, perfumes, lubricants, UV stabilizers, antioxidants or surfactants. The term "auxiliaries and additives" according to the invention means any pharmacologically acceptable and therapeutically meaningful substance which is not a pharmaceutically active substance but can be formulated together with the pharmaceutically active substance in a pharmaceutical composition to influence, in particular to improve, qualitative properties of the pharmaceutical composition. Preferably, the auxiliaries and/or additives do not develop any significant or at least any undesirable pharmacological effect with regard to the intended treatment.

Preferred compositions according to the invention relate to a pharmaceutical composition which comprises a nanostructured carrier system according to the invention, at least one pharmaceutically active substance and suitable auxiliaries and additives.

Preferred compositions according to the invention contain organic polymer particles having an average diameter $D_{50}$ of less than 10 μm, in particular less than 1 μm. $D_{50}$ means that 50% by volume of the particles are smaller than the value given for $D_{50}$. The $D_{50}$ value may be determined for the purposes of the present description by light scattering or by microscopy, for example by transmission electron microscopy or by scanning electron microscopy.

Particularly preferred compositions according to the invention are those with organic polymer particles having particle diameters in the range from 50 to 999 nm. The particle diameters refer to the primary particles and may be determined for the purposes of the present description by (dynamic) light scattering ((D)LS), by nanosize tracking analysis (NTA), or by electron microscopy, e.g., by transmission electron microscopy or by scanning electron microscopy.

The organic polymer particles may be present in the compositions of the invention as powders in solid form or they may be dispersed in hydrophilic solvents, the particles being present in the dispersing medium in liquid form or especially in solid form.

In preferred compositions of the invention, the organic polymer particles form a dispersed phase in a liquid containing water and/or water-miscible compounds.

In particularly preferred compositions according to the invention, the organic polymer particles are dispersed in the hydrophilic liquid.

In a further preferred embodiment of the compositions according to the invention, the particles of the finely divided organic polymer are present in solid form and the particles are enveloped by the poly(oxazoline).

The organic polymer used according to the invention is a selected polymer as defined above or a mixture of such polymers.

Examples of classes of substances which can form the backbone of the polymer used according to the invention are α-olefins, such as polyolefins derived from ethylene and/or propylene and/or from vinylaromatics, such as styrene-derived polyvinylaromatics and/or vinyl esters of aliphatic carboxylic acids, such as polyvinyl esters derived from vinyl acetate and/or polyesters derived from organic dicarboxylic acids and organic diols and/or from organic hydroxycarboxylic acids, polycarbonates, polyamides derived from organic dicarboxylic acids and organic diamines and/or from organic aminocarboxylic acids, polymers derived from ethylenically unsaturated carboxylic acids and/or their esters and/or their amides, such as polyacrylic acid, polymethacrylic acid, polyacrylate, polymethacrylate, polyacrylamide or polymethacrylamide, polymers derived from vinyl esters of saturated carboxylic acids or their derivatives, such as polyvinyl acetate or polyvinyl alcohol, polyimides derived from imide-forming tetracarboxylic acids and diamines, polynitriles derived from ethylenically unsaturated nitriles, polysulfonic acids derived from ethylenically unsaturated organic sulfonic acids, polyketones or polysulfones derived from dihaloaryl ketones or sulfones, polyalkylene glycols, polyurethanes derived from organic diisocyanates and organic diols, from alpha-aminocarboxylic acids derived proteins, naturally occurring polymeric carbohydrates and their chemically modified polymeric derivatives, such as cellulose or cellulose ethers, as well as naturally occurring or synthetically produced nucleic acids, such as deoxyribonucleic acids, ribonucleic acids or their chemically modified polymeric derivatives The polymers used according to the invention may be present as linear polymers or they may be graft, comb and star polymers, dendrimers, ladder polymers, ring-shaped polymers, polycatenanes and polyrotaxanes.

The solubility of the polymers used according to the invention can be influenced by copolymerization with suitable monomers and/or by functionalization. Those skilled in the art are familiar with such techniques.

The organic polymers used according to the invention may comprise a wide molecular weight range. Typical molar masses ($M_n$) are in the range from 2,000 to 500,000 g/mol, in particular from 5,000 to 49,900 g/mol. These molecular weights can be determined by $^1$H NMR spectroscopy of the dissolved polymer. In particular, an analytical ultracentrifuge or chromatographic methods, such as size exclusion chromatography, can be used to determine the molecular weights.

Preferably used organic polymers have a number average molecular weight in the range of 5,000 to 20,000 g/mol, determined by $^1$H-NMR spectroscopy or by using an analytical ultracentrifuge.

The proportion of the organic polymer in the composition of the present invention may cover a wide range. When the organic polymer is dispersed in a dispersion medium, its content in the total composition is generally 0.5 to 20 wt %, preferably 1 to 5 wt %. If the organic polymer is present in particle form together with the poly(oxazoline), for example as a powdered solid, its proportion in the overall composition is generally from 0.1 to 30 wt %, preferably from 0.5 to 10 wt %.

The preparation of the organic polymer used according to the invention can be carried out by the usual polymerization methods. Examples of these are the bulk polymerization, polymerization in solution or emulsion, or suspension polymerization. These procedures are known to the person skilled in the art.

Among the most preferred organic polymers used is the group of polyesters. These are generally polycondensates derived from aliphatic or cycloaliphatic diols and from aliphatic, cycloaliphatic and/or aromatic dicarboxylic acids or their polyester-forming derivatives, such as their dialkyl esters. They may also be polycondensates derived from aliphatic or cycloaliphatic hydroxymonocarboxylic acids or their polyester-forming derivatives, such as hydroxymonocarboxylic acid alkyl esters.

Preferred polyesters include the polyesters derived from aliphatic diols and from aliphatic dicarboxylic acids or from aliphatic dicarboxylic acid alkyl esters and the polyesters derived from aliphatic hydroxymonocarboxylic acids or from aliphatic hydroxymonocarboxylic acid alkyl esters.

Particular preference is given to using polyhydroxyalkanoate(s), and very particular preference to using lactic acid homo-(PLA) or copolymer(s).

A most preferred polyester used is the lactic acid-glycolic acid copolymer (PLGA).

Further very preferred organic polymers are polymers derived from ethylenically unsaturated carboxylic acids and/or their esters and/or their amides, in particular polyacrylic acid esters and/or homopolymers or copolymers derived from polymethacrylic acid esters, very particularly preferably alkyl acrylate-methyl acrylate copolymers.

The compositions according to the invention contain one or more water-soluble poly(oxazoline)s. The amount of poly(oxazoline)s, based on the total amount of the composition according to the invention, is usually 0.1 to 30 wt %.

Poly(oxazoline)s are known compounds. These are usually prepared by cationic ring-opening polymerization of oxazolines, preferably 2-oxazolines, in solution and in the presence of an initiator. Examples of initiators are electrophiles, such as salts or esters of aromatic sulfonic acids or carboxylic acids or salts or esters of aliphatic sulfonic acids or carboxylic acids or aromatic halogen compounds. It is also possible to use polyfunctional electrophiles as initiators. In addition to linear poly(oxazoline)s, branched or star-shaped molecules can also be formed. Examples of preferred initiators are esters of arylsulfonic acids, such as methyl tosylate, esters of alkanesulfonic acids, such as trifluoromethanesulfonic acid, or mono- or dibromobenzene. The polymerization is usually carried out in a polar aprotic solvent, for example in acetonitrile.

As oxazolines for the preparation of the poly(oxazoline)s used in the invention, 2-oxazolines (4,5-dihydrooxazoles) with a C=N double bond between the carbon atom 2 and the nitrogen atom are used. These may be substituted on the 2-, 4- and/or 5-carbon atom and/or on the 3-nitrogen atom, preferably on the 2-carbon atom and/or on the 3-nitrogen atom.

Preference is given to using 2-oxazolines which contain a substituent at the 2-position. Examples of such substituents are methyl or ethyl.

In addition to the 2-oxazolines, it is also possible to use small amounts of further monomers copolymerizable with 2-oxazolines in the preparation of the water-soluble poly(oxazoline)s used according to the invention.

The water-soluble poly(oxazoline)s used according to the invention generally contain at least 80 wt %, in particular at least 90 wt % and most preferably at least 95 wt %, based on their total mass, of recurring structural units of formula I and/or of formula II

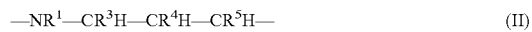

wherein
$R^1$ is a radical of the formula —CO—$R^2$,
$R^3$, $R^4$ and $R^5$, independently of one another, denote hydrogen, methyl, ethyl, propyl or butyl, $R^2$ is selected from the group consisting of hydrogen, methyl, ethyl, —$C_mH_{2m}$—X or —($C_nH_{2n}$—O)$_o$—($C_pH_{2p}$—O)$_q$—$R^6$, R⁶ is hydrogen or $C_1$-$C_6$-alkyl, in particular methyl or very particularly preferably hydrogen, m is an integer from 1 to 6, X is selected from the group consisting of hydroxyl, alkoxy, amino, N-alkylamino, N,N-dialkylamino, carboxyl, carboxylic acid ester, sulfonyl, sulfonic acid ester or carbamate, n and p are independently integers from 2 to 4, where n is not equal to p, n is preferably 2 and p is preferably 3, and o and q are independently integers from 0 to 60, especially 1 to 20 and most preferably 2 to 10, wherein at least one of o or q is not 0.

Preferred water-soluble poly(oxazoline)s used according to the invention are those in which $R^2$ is hydrogen, methyl or ethyl and $R^3$ to $R^5$ are hydrogen or in which $R^2$ is hydrogen, methyl or ethyl and two of the radicals $R^3$ to $R^5$ are hydrogen and one of $R^3$ to $R^5$ is methyl or ethyl.

The molar mass of the poly(oxazoline)s used according to the invention is generally from 5,000 to 500,000 g/mol, in particular from 5,000 to 20,000 g/mol. The molecular weight is determined for the purposes of the present description by $^1$H-NMR analysis.

Very particularly preferred compositions according to the invention comprise a water-soluble poly(oxazoline) which has at least 90 wt %, in particular at least 95 wt %, based on the total mass thereof, of recurring structural units of the formula I in which $R^2$ is methyl or ethyl.

Further preferred compositions according to the invention contain, in addition to the finely divided organic polymer, one or more pharmaceutically active substances.

The compositions according to the invention can be prepared by precipitation, preferably by nanoprecipitation. For this purpose, the organic polymers used according to the invention, which are hydrophilic due to the presence of polar groups, are dissolved in a water-immiscible solvent, such as dichloromethane, or in a water-miscible solvent, such as acetone or ethyl acetate. This solution is dripped into a hydrophilic dispersing medium containing a water-soluble poly(oxazoline), preferably into water-soluble poly(2-oxazoline)-containing water or into a water-soluble poly(2-oxazoline)-containing mixture of water and methanol or ethanol. This is preferably carried out with vigorous stirring. This promotes the production of smaller particles. The organic polymer is precipitated in the dispersion medium in finely divided form.

Alternatively, the compositions of the invention may also be produced by emulsification, preferably by nanoemulsion. For this purpose, the organic polymers used according to the invention, which are hydrophilic due to the presence of polar groups, are dissolved in a water-immiscible solvent, such as dichloromethane, or in a water-miscible solvent, such as acetone or ethyl acetate. This solution is combined with a hydrophilic dispersing medium containing a water-soluble poly(oxazoline), preferably water-soluble poly(2-oxazoline)-containing water or water-soluble poly(2-oxazoline)-containing mixture of water and methanol or ethanol preferably form two liquid phases. Subsequently, this mixture is emulsified by energy input, preferably by sonicating.

In addition to the organic polymer, one or more active ingredients and/or one or more auxiliaries and additives may be present during its dispersion in the dispersing medium. Alternatively, these agents and/or adjuvants and additives may be added after dispersing the organic polymer in the hydrophilic liquid.

Typically, polyvinyl alcohol or polyethlyene-polypropylene block copolymers such as Pluronic® F127 or Pluronic® F68, or polyoxyethylene sorbitan monooleate such as Tween® 80 have been used in the manufacture of particles dispersed in hydrophilic liquids organic polymers. The compositions of the invention are characterized by increased stability compared to these known compositions.

The separation of the polymer particles and the poly(oxazoline) stabilizer from the hydrophilic liquid can take place in different ways. Examples are centrifugation, ultrafiltration or dialysis.

Particular preference is given to working up the polymer particles, which may optionally additionally contain an active ingredient and/or auxiliaries and additives, and the poly(oxazoline) stabilizer from the hydrophilic liquid by freeze-drying. It has surprisingly been found that the poly(oxazoline)es act as cryoprotectants. Compared to previously used sugar-based cryoprotectants, such as HEPES buffered glucose, glucose or sucrose, no further work-up step is necessary in the poly(oxazoline) stabilized dispersions after freeze-drying, for example by centrifugation, since no cytotoxicity, hemolysis or other known immune reactions are triggered by the finely divided polymers obtained according to the invention.

The polymer dispersion prepared according to the invention can be further purified after the preparation. Common methods include purification by dialysis, by ultrafiltration, by filtration or by centrifugation.

By means of filtration, particles, such as aggregates, but also endotoxins, non-encapsulated active substances or auxiliaries or bacterial impurities can be separated from the dispersion. The particle concentration may change.

By means of dialysis, solvents or dissolved molecules can be separated from the dispersion. With regard to the dispersed particles, the process is largely independent on the particle size. However, in carrying out the dialysis, the concentration of the dispersed particles decreases, and the process is relatively time-consuming.

Purification by centrifugation also allows solvents or dissolved molecules to be separated from the dispersion. However, the concentration of the dispersed particles also decreases with this method. In addition, only dispersions with nanoparticles of larger diameter, for example of more than 150 nm, can be treated, and the particles can be affected thereby. Furthermore, redispersing the particles thus obtained can be difficult.

When using the poly(oxazoline)s according to the invention in the purification of polymer dispersions, it has surprisingly been found that the hitherto known disadvantages found with dialysis, with centrifugation and with purification by means of filters occur only to a considerably reduced extent or even disappear completely.

The invention also relates to the use of water-soluble poly(oxazoline) for the stabilization of organic polymer particles selected from the group of polyolefins, polyvinylaromatics, polyvinyl esters, polyesters, polyamides, polyimides, polycarboxylic acids, polycarboxylic acid esters, polycarboxylic acid amides, polynitriles, polysulfonic acids, polyketones, polysulfones, polymeric polyols, polyurethanes, proteins, polymeric carbohydrates, nucleic acids or a mixture of two or more of these polymers in a liquid containing water and/or water-miscible compounds.

The invention further relates to the use of water-soluble poly(oxazoline) for the stabilization of organic polymer particles selected from the group of polyolefins, polyvinylaromatics, polyvinyl esters, polyesters, polyamides, polyimides, polycarboxylic acids, polycarboxylic acid esters, polycarboxylic acid amides, polynitriles, polysulfonic acids, polyketones, polysulfones, polymeric polyols, polyurethanes, proteins, polymeric carbohydrates, nucleic acids or from a mixture of two or more of these polymers in the freeze-drying.

Particular preference is given to using suspensions of the finely divided organic polymer in a hydrophilic liquid.

Moreover, the invention relates to the use of water-soluble poly(oxazoline) as stabilizers in the preparation or in the processing of organic polymer particles selected from the group of polyolefins, polyvinylaromatics, polyvinyl esters, polyesters, polyamides, polyimides, polycarboxylic acids, polycarboxylic acid esters, polycarboxylic acid amides, polynitriles, polysulfonic acids, polyketones, polysulfones, polymeric polyols, polyurethanes, proteins, polymeric carbohydrates, nucleic acids or a mixture of two or more of these polymers in a hydrophilic liquid.

Particular preference is given to using the work-up methods of dialysis, centrifugation or filtration.

Finally, the invention relates to the use of water-soluble poly(oxazoline) for stabilizing powdered organic polymer particles selected from the group of polyolefins, polyvinylaromatics, polyvinyl esters, polyesters, polyamides, polyamides, polycarboxylic acids, polycarboxylic acid esters, polycarboxylic acid amides, polynitriles, polysulfonic acids, polyketones, polysulfones, polymeric polyols, polyurethanes, proteins, polymeric carbohydrates, nucleic acids or a mixture of two or more of these polymers.

The following examples illustrate the invention without limiting it.

EXAMPLE 1

Preparation of poly(2-oxazoline)s ($PD_x$)

The synthesis of poly(2-oxazoline)s has already been described in the literature (see, for example, Wiesbrock, F. et al., *Macromolecular Rapid Communications* 2004, 25, 1895-1899). The procedure is therefore exemplified for poly(2-ethyl-2-oxazoline) having a degree of polymerization (DP) of 61 ($P(EtOx)_{61}$).

In a microwave reaction vessel 2-ethyl-2-oxazoline (6.06 mL, 60.0 mmol), methyl tosylate (0.15 mL, 0.1 mmol) and acetonitrile (8.79 mL) were mixed under inert conditions. The reaction vessel was then heated to 140° C. in a synthesis microwave for 14 minutes. Subsequently, the reaction was terminated by the addition of 0.5 mL of deionized water and stirred overnight at room temperature. The resulting solution was purified by diluting with dichloromethane and then precipitated in excess ice-cold diethyl ether. The precipitated polymer was then filtered off and dissolved in dichloromethane. The solvent was then removed on a rotary evaporator and the polymer was dried under high vacuum until completely free of solvent. The final product was a crystalline, white solid.

$^1$H-NMR ($CDCl_3$, 300 MHz): δ=4.34 (0.1H, s, backbone-OH), 3.44 (4.0H, s, backbone), 3.02 (0.3H, s, $CH_3$-backbone), 2.4 (1.7H, m, $CH_2$ (EtOx)), 1.11 (2.5H, s, $CH_3$ (EtOx)) ppm.

SEC (eluent: DMAc[1], 0.21% LiCl, PS[2] standard): $M_n$=11,200 g mol$^{-1}$, $M_w$=12,200 g mol$^{-1}$, Đ=1.09.

FIG. 1 shows the $^1$H NMR (300 MHz, $CDCl_3$) plot of $P(EtOx)_{61}$.

FIG. 2 shows the size exclusion chromatogram (DMAc[1], 0.21% LiCl, PS[2] calibration) of $P(EtOx)_{61}$.

[1] DMAc=dimethylacetamide
[2] PS=polystyrene

EXAMPLE 2

Freeze-Drying Experiments

PLGA[3] nanoparticles were prepared by nanoprecipitation (see Example 3) and characterized by dynamic light scattering in terms of size (particle diameter, z-average) and size distribution (PDI). Following this characterization, a certain amount of cryoprotectant was added to the nanoparticle suspension at various concentrations. The suspensions were frozen in a −80° C. freezer and then freeze-dried (24 h, −56° C., 0.01 mbar). About 2 mg of the resulting powder was resuspended in 1 mL ultrapure water and then characterized again with dynamic light scattering for particle diameter (z-average) and PDI. The ratios were determined by dividing the values taken after lyophilization by those determined immediately after preparation.

TABLE 1

Results of the PLGA lyophilization experiments[3] Nanoparticles with different concentrations of $P(EtOx)_{61}$ as cryoprotectant.

| | Concentration Cryoprotectant [%] | | | | | | |
|---|---|---|---|---|---|---|---|
| | 0 | 0.05 | 0.10 | 0.50 | 1.00 | 2.50 | 5.00 |
| Size after preparation [nm] | | | | 88.9 ± 0.8 | | | |
| Size after lyophilization [nm] | 2131.2 + 1090.4 | 171.2 ± 12.7 | 130.5 ± 19.1 | 123.5 ± 24.3 | 133.4 ± 28.6 | 129.8 ± 20.1 | 138.5 ± 31.6 |
| Size ratio | 23.9 | 1.9 | 1.5 | 1.4 | 1.5 | 1.5 | 1.6 |
| PDI after preparation | | | | 0.095 ± 0.007 | | | |
| PDI after lyophilization | 0.669 ± 0.131 | 0.387 ± 0.050 | 0272 ± 0.046 | 0.190 ± 0.065 | 0.217 ± 0.049 | 0.230 ± 0.064 | 0.240 ± 0.064 |
| PDI ratio | 7.0 | 4.1 | 2.9 | 2 | 2.3 | 2.4 | 2.5 |
| Zeta potential after preparation [mV] | | | | −29.6 ± 0.2 | | | |
| Zeta potential after lyophilization [mV] | −29.7 ± 4.4 | −29.2 ± 2.5 | −30.9 ± 9.4 | −21.1 ± 6.7 | −19.7 ± 12.1 | −23.1 ± 10.7 | −23.9 ± 7.9 |
| Zeta potential ratio | 1.0 | 1.0 | 1.0 | 0.7 | 0.7 | 0.8 | 0.8 |

EXAMPLE 3a

Production of Nanoparticle Suspensions by Nanoprecipitation 5 mg PLGA[3] was dissolved in 2.5 mL acetone and then added by syringe pump at a defined rate with constant stirring into a vessel with 4.5 mL of an aqueous $P(EtOx)_{61}$ solution. The organic solvent was then evaporated overnight with constant stirring and the nanoparticles were characterized in terms of their particle diameter and PDI.

TABLE 2

Results of the production of PLGA[3] nanoparticles by nanoprecipitation with different concentrations of $P(EtOx)_n$ as surfactant.

| | Concentration of surfactant [mg mL$^{-1}$] | | | |
|---|---|---|---|---|
| | 0 | 0.3 | 0.5 | 1 |
| Size [nm] | 98.0 ± 9.9 | 118.0 ± 0.7 | 122.2 ± 5.9 | 116.6 ± 5.2 |
| PDI | 0.103 ± 0.020 | 0.093 ± 0.007 | 0.153 ± 0.043 | 0.086 ± 0.017 |

[3]PLGA = lactic acid-glycolic acid copolymer

EXAMPLE 3b

Preparation of Nanoparticle Suspensions by Nanoemulsion

A defined amount of $P(EtOx)_{61}$ was dissolved in 1 mL ultrapure water. 10 mg PLGA[3] was dissolved in 0.5 mL of ethyl acetate, carefully pipetted onto the surfactant solution and then treated with the ultrasonic finger (power: 40 W, cycle: 100%, amplitude: 100%, time: 10 sec). Subsequently, the particle suspension was diluted by a factor of 10 with ultrapure water and stirred overnight at room temperature to evaporate the organic solvent and the nanoparticles were characterized in terms of their particle diameter and the PDI.

TABLE 3

Results of the preparation of PLGA[3] nanoparticles using nanoemulsion with different concentrations of $P(EtOx)_{61}$ as surfactant.

| Concentration of surfactant [%] | 0 | 0.3 | 0.5 | 1 |
|---|---|---|---|---|
| Size [nm] | 231.5 ± 15.3 | 448.9 ± 21.2 | 460.5 ± 48.5 | 217.4 ± 6.1 |
| PDI | 0.353 ± 0.010 | 0.383 ± 0.039 | 0.463 ± 0.061 | 0.164 ± 0.015 |

EXAMPLE 4a

Influence of the DP of Poly(2-Oxazoline) on the Size of the Polymer Nanoparticles after Preparation by Nanoprecipitation 5 mg PLGA[3] was dissolved in 2.5 mL acetone and then added by syringe pump at a defined rate with constant stirring into a vessel with 4.5 mL of an aqueous $P(EtOx)_n$ or $P(MeOx)_n$ solution. The organic solvent was then evaporated overnight with constant stirring and the nanoparticles were characterized for their particle diameter and PDI by dynamic light scattering. A portion of the suspension was frozen in the −80° C. freezer and then lyophilized overnight. Approximately 2 mg of the resulting powder was then resuspended in 1 mL ultrapure water and recharacterized. The ratio of the values was calculated by dividing the corresponding readings after lyophilization by those after preparation.

TABLE 4

Results of the preparation of PLGA[3] nanoparticles by nanoprecipitation with $P(EtOx)_n$ as surfactant in a concentration of 1% (w/v).

| | DP $P(EtOx)_n$ | | | |
|---|---|---|---|---|
| | 25 | 61 | 107 | 184 |
| Size after preparation [nm] | 157.5 ± 7.2 | 118.0 ± 0.7 | 164.4 ± 11.5 | 172.5 ± 10.8 |
| Size after lyophilization [nm] | 272.1 ± 167.8 | 134.5 ± 4.7 | 167.1 ± 15.7 | 173.4 ± 13.8 |
| Size ratio | 1.7 | 1.4 | 1.02 | 1.0 |
| PDI after preparation | 0.071 ± 0.009 | 0.093 ± 0.007 | 0.076 ± 0.007 | 0.074 ± 0.010 |
| PDI after lyophilization | 0.261 ± 0.054 | 0.147 ± 0.052 | 0.114 ± 0.007 | 0.112 ± 0.002 |
| PDI ratio | 3.7 | 1.6 | 1.5 | 1.5 |

[3]PLGA = lactic acid-glycolic acid copolymer

TABLE 5

Results of the production of PLGA[3] nanoparticles by nanoprecipitation
with P(MeOx)$_n$ as surfactant in a concentration of 1% (w/v).

| | DP P(MeOx)$_n$ | | | |
|---|---|---|---|---|
| | 25 | 57 | 100 | 211 |
| Size after preparation [nm] | 169.8 ± 9.7 | 195.8 ± 6.0 | 172.9 ± 18.8 | 181.8 ± 5.9 |
| Size after lyophilization [nm] | 299.4 ± 114.1 | 223.0 ± 36.6 | 181.6 ± 27.0 | 173.4 ± 15.9 |
| Size ratio | 1.8 | 1.1 | 1.1 | 1.0 |
| PDI after preparation | 0.059 ± 0.006 | 0.069 ± 0.009 | 0.069 ± 0.015 | 0.124 ± 0.092 |
| PDI after lyophilization | 0.343 ± 0.069 | 0.125 ± 0.065 | 0.137 ± 0.023 | 0.108 ± 0.026 |
| PDI ratio | 5.8 | 1.8 | 2.0 | 0.9 |

[3] PLGA=lactic acid-glycolic acid copolymer

EXAMPLE 4b

Influence of the DP of Poly(2-Oxazoline) on the Particle Size of the Polymer Nanoparticles after Preparation by Means of Nanoemulsion A defined amount of P(EtOx)$_n$ or P(MeOx)$_n$ was dissolved in 1 mL ultrapure water. 10 mg PLGA[3] was dissolved in 0.5 mL of ethyl acetate, carefully pipetted onto the surfactant solution and then treated with the ultrasonic finger (power: 40 W, cycle: 100%, amplitude: 100%, time: 10 seconds). Subsequently, the particle suspension was diluted by a factor of 10 with ultrapure water and stirred overnight at room temperature to evaporate the organic solvent and the nanoparticles were characterized in terms of their particle diameter and the PDI. A portion of the suspension was frozen in the −80° C. freezer and then lyophilized overnight. Approximately 2 mg of the particles was then resuspended in 1 mL ultrapure water and recharacterized. The ratio of the values was calculated by dividing the corresponding readings after lyophilization by those after preparation.

TABLE 6

Results of the preparation of PLGA[3] nanoparticles using nanoemulsion
with P(EtOx)$_n$ as surfactant in a concentration of 1% (w/v).

| | DP P(EtOx)n | | | |
|---|---|---|---|---|
| | 25 | 61 | 107 | 184 |
| Size after preparation [nm] | 808.1 ± 362.7 | 217.4 ± 6.1 | 230.2 ± 18.5 | 194.2 ± 10.3 |
| Size after lyophilization [nm] | nd | 204.4 ± 4.3 | 213.1 ± 12.8 | 179.2 ± 13.1 |
| Size ratio | nd | 0.9 | 0.9 | 0.9 |
| PDI after preparation | 0.754 ± 0.426 | 0.164 ± 0.015 | 0.146 ± 0.047 | 0.086 ± 0.011 |
| PDI after lyophilization | nd | 0.100 ± 0.017 | 0.113 ± 0.010 | 0.102 ± 0.008 |
| PDI ratio | nd | 0.6 | 0.8 | 1.2 | nd: not determined.

TABLE 7

Results of the preparation of PLGA[3] nanoparticles using nanoemulsion
with P(MeOx)$_n$ as surfactant in a concentration of 1% (w/v).

| | DP P(MeOx)$_n$ | | | |
|---|---|---|---|---|
| | 25 | 57 | 100 | 211 |
| Size after preparation [nm] | 803.7 ± 231.8 | 159.7 ± 4.0 | 273.2 ± 20.7 | 200.5 ± 5.3 |
| Size after lyophilization [nm] | nd | 164.4 ± 6.7 | 269.9 ± 32.5 | 191.8 ± 7.2 |
| Size ratio | nd | 1.0 | 1.0 | 1.0 |
| PDI after preparation | 0.289 | 0.086 ± 0.003 | 0.165 ± 0.007 | 0.080 ± 0.004 |
| PDI after lyophilization | nd | 0.108 ± 0.019 | 0.185 ± 0.083 | 0.100 ± 0.013 |
| PDI ratio | nd | 1.3 | 1.1 | 1.3 |

[3] PLGA = lactic acid-glycolic acid copolymer
nd: not determined.

EXAMPLE 5

Nanoparticles from Different Shell Polymers 100 mg P(EtOx)$_n$ or P(MeOx)$_n$ was dissolved in 1 mL ultrapure water. 10 mg of shell polymer was dissolved in 0.5 mL of ethyl acetate, carefully pipetted onto the surfactant solution and then treated with the ultrasonic finger (power: 40 W, cycle: 100%, amplitude: 100%, time: 10 seconds). Subsequently, the particle suspension was diluted by a factor of 10 with ultrapure water and stirred overnight at room temperature to evaporate the organic solvent and the nanoparticles were characterized in terms of their particle diameter and the PDI. The nanoparticles were purified differently as described in the Table. Thereafter, all resulting particle suspensions were frozen in the −80° C. freezer and then lyophilized overnight. Approximately 2 mg of the powder was then resuspended in 1 mL ultrapure water and recharacterized. The ratio of the values was calculated by dividing the corresponding readings after lyophilization by those after preparation.

TABLE 8

Properties of nanoparticles from different shell polymers using P(EtOx)$_{61}$ or P(MeOx)$_{57}$ as surfactant after preparation by nanoemulsion.

| Coating polymer | Surfactant | Size [d, nm] | PDI | Zeta Potential [mV] |
|---|---|---|---|---|
| PLGA[3)] | P(EtOx)$_{61}$ | 214.9 ± 1.5 | 0.147 ± 0.030 | −33.0 ± 0.9 |
|  | P(MeOx)$_{57}$ | 155.8 ± 0.9 | 0.087 ± 0.023 | −37.9 ± 0.5 |
|  | None | n.a. | n.a. | n.a. |
| Eudragit ® RS 100[4)] | P(EtOx)$_{61}$ | 214.0 ± 0.7 | 0.063 ± 0.018 | 35.7 ± 0.4 |
|  | P(MeOx)$_{57}$ | 244.3 ± 2.5 | 0.081 ± 0.012 | 42.1 ± 1.7 |
|  | None | 101.6 ± 0.5 | 0.246 ± 0.020 | 58.6 ± 0.4 |
| P(MMA$_7$-co-MAEMA$_{32}$)[b)] | P(EtOx)$_{61}$ | 155.2 ± 2.8 | 0.165 ± 0.012 | 32.3 ± 0.1 |
|  | P(MeOx)$_{57}$ | 162.9 ± 1.3 | 0.138 ± 0.028 | 33.6 ± 1.4 |
|  | None | 176.2 ± 2.4 | 0.191 ± 0.012 | 49.1 ± 0.4 | n.a.: not available (not available because the nanoparticles were too strongly aggregated).

TABLE 9

Properties of the nanoparticles from different shell polymers using P(EtOx)$_{6i}$ or P(MeOx)$_{57}$ as surfactant after purification and lyophilization. P(MeOx)$_{57}$ is a poly(2-methyl-2-Oxazoline) with a degree of polymerization (DP) of 57.

P(MMA$_{97}$-co-MAEMA32)[5)]

| Surfactant | P(EtOx)$_{61}$ | | P(MeOx)$_{57}$ | | None | |
|---|---|---|---|---|---|---|
| Purification method | Size [d, nm] | PDI | Size [d, nm] | PDI | Size [d, nm] | PDI |
| After preparation | 155.2 ± 2.8 | 0.165 ± 0.012 | 162.9 ± 1.3 | 0.138 + 0.028 | 176.2 ± 2.4 | 0.191 ± 0.012 |
| Lyophilization without purification | 172.2 ± 2.7 | 0.215 ± 0.021 | 157.5 ± 1.9 | 0.109 + 0.026 | n.a. | n.a. |
| Centrifugation and resuspension in 1 mL ultrapure water | 229.2 ± 14.9 | 0.330 ± 0.019 | 294.7 ± 67.1 | 0.375 ± 0.033 | 325.8 ± 88.1 | 0.362 ± 0.034 |
| Centrifugation and resuspension in 1 mL 0.5% POx solution | 175.4 ± 2.3 | 0.258 ± 0.035 | 179.7 ± 3.8 | 0.128 ± 0.083 | 253.4 ± 4.1* | 0.278 ± 0.042* |
| Syringe filtration | n.a. | n.a. | 211.6 ± 3.1 | 0.269 ± 0.032 | n.a. | n.a. |

Eudragit ® RS100[4)]

| Surfactant | P(EtOx)$_{61}$ | | P(MeOx)$_{57}$ | | None | |
|---|---|---|---|---|---|---|
| Purification method | Size [d, nm] | PDI | Size [d, nm] | PDI | Size [d, nm] | PDI |
| After preparation | 214.0 ± 0.7 | 0.063 ± 0.018 | 244.3 ± 2.5 | 0.081 ± 0.012 | 101.6 ± 0.5 | 0.246 ± 0.020 |
| Lyophilization without purification | 217.2 ± 2.2 | 0.080 ± 0.024 | 247.3 ± 4.3 | 0.086 ± 0.038 | n.a. | n.a. |
| Centrifugation and resuspension in 1 mL ultrapure water | 239.3 ± 1.7 | 0.105 ± 0.037 | 315.9 ± 8.3 | 0.220 + 0.044 | n.a. | n.a. |
| Centrifugation and resuspension in 1 mL 0.5% POx solution | 223.3 ± 1.5 | 0.069 ± 0.026 | 252.0 ± 3.4 | 0.105 ± 0.039 | n.a. | n.a. |
| Syringe filtration | 220.4 ± 4.4 | 0.062 ± 0.042 | 257.5 ± 3.7 | 0.068 ± 0.033 | n.a. | n.a. | n.a.: Not available (not available because the nanoparticles were too strongly aggregated).

TABLE 10

Ratios of the properties of the nanoparticles from different shell polymers using P(EtOx)$_{61}$ or P(MeOx)$_{57}$ as surfactant after purification and lyophilization. P(MeOx)$_{57}$ is a poly(2-methyl-2-Oxazoline) with a degree of polymerization (DP) of 57.

| Surfactant | P(EtOx)$_{61}$ | | P(MeOx)$_{57}$ | | None | |
|---|---|---|---|---|---|---|
| Purification method | Size ratio | PDI ratio | Size ratio | PDI ratio | Size ratio | PDI ratio |
| P(MMA$_{97}$-co-MAEMA32)[5] | | | | | | |
| Lyophilization without purification | 1.11 | 1.30 | 0.97 | 0.79 | n.a. | n.a. |
| Centrifugation and resuspension in 1 mL ultrapure water | 1.48 | 2.00 | 1.01 | 1.06 | 1.85 | 1.90 |
| Centrifugation and resuspension in 1 mL 0.5% POx solution | 1.13 | 1.56 | 1.10 | 0.93 | 1.44* | 1.46* |
| Syringe filtration | n.a. | n.a. | 1.30 | 1.95 | n.a. | n.a. |
| Eudragit® RS100[4] | | | | | | |
| Lyophilization without purification | 1.01 | 1.27 | 1.01 | 1.06 | n.a. | n.a. |
| Centrifugation and resuspension in 1 mL ultrapure water | 1.12 | 1.67 | 1.29 | 2.71 | n.a. | n.a. |
| Centrifugation and resuspension in 1 mL 0.5% POx solution | 1.04 | 1.10 | 1.03 | 1.30 | n.a. | n.a. |
| Syringe filtration | 1.03 | 0.98 | 1.05 | 0.84 | n.a. | n.a. |

[3]PLGA = lactic acid-glycolic acid copolymer
[4]Eudragit® RS 100 = methyl methacrylate (2-(N,N,N-trimethylammonium))methacrylate-ethyl acrylate copolymer
[5]P(MMAg$_7$-co-MAEMA$_3$2) = 2-(N-methylaminoethyl)methacrylate-methyl acrylate copolymer
n.a.: Not available (not available because the nanoparticles were too strongly aggregated).

EXAMPLE 6

Influence of the Purification on the Size of the Nanoparticles 5 mg PLGA[3] was dissolved in 2.5 mL acetone and then added by syringe pump at a defined rate with constant stirring into a vessel with 4.5 mL of an aqueous P(EtOx)$_{61}$ solution. The organic solvent was then evaporated overnight with constant stirring and the nanoparticles were characterized in terms of their particle diameter and PDI. The nanoparticles were purified differently as described in the Table. Thereafter, all resulting particle suspensions were frozen in the −80° C. freezer and then lyophilized overnight. Approximately 2 mg of the powder was then resuspended in 1 mL ultrapure water and recharacterized. The ratio of the values was calculated by dividing the corresponding readings after lyophilization by those after preparation.

TABLE 11

Properties of PLGA[3] nanoparticles using P(EtOx)$_6$i or P(MeOx)$_{57}$ as surfactant after purification and lyophilization.

| | Surfactant | | | |
|---|---|---|---|---|
| Purification method before lyophilization | P(EtOx)$_{61}$ | | P(MeOx)$_{57}$ | |
| | Size [d, nm] | PDI | Size [d, nm] | PDI |
| After preparation | 157.7 ± 1.3 | 0.102 ± 0.017 | 201.7 ± 4.2 | 0.062 ± 0.029 |
| Lyophilization without purification | 1262 ± 1182 | 0.714 ± 0.201 | 213.5 ± 3.1 | 0.067 ± 0.010 |
| Centrifugation and resuspension in 1 mL ultrapure water | 898 ± 1062 | 0.549 ± 0.305 | 206.7 ± 3.1 | 0.111 ± 0.034 |
| Syringe filtration and addition of 1 ml. 0.5% POx solution | 165.1 ± 1.0 | 0.172 ± 0.044 | 189.6 ± 1.2 | 0.068 ± 0.018 |
| Syringe filtration | 1075 ± 111.6 | 0.948 ± 0.100 | 190.6 ± 1.5 | 0.101 ± 0.019 |

TABLE 12

Ratios of properties of PLGA[3)]-nanoparticles using P(EtOx)$_6$i
or P(MeOx)$_{57}$ as a surfactant after purification and lyophilization.

| Purification method | Additives | | | |
|---|---|---|---|---|
| | P(EtOx)$_{61}$ | | P(MeOx)$_{57}$ | |
| | Size ratio | PDI ratio | Size ratio | PDI ratio |
| Lyophilization without purification | 8.00 | 7.00 | 1.06 | 1.08 |
| Centrifugation and resuspension in 1 mL ultrapure water | 5.69 | 5.38 | 1.02 | 1.79 |
| Syringe filtration and addition of 1 mL 0.5% PO$_x$ solution | 1.05 | 1.69 | 0.94 | 1.10 |
| Syringe filtration | 6.82 | 9.29 | 0.94 | 1.63 |

[3)]PLGA = lactic acid-glycolic acid copolymer
n.a.: not available (not available because the nanoparticles were too strongly aggregated).

EXAMPLE 7

Encapsulation of Nile Red

From 10 mg of PLGA[3)] and 0.1 mg of Nile Red from a 1 mg mL$^{-1}$ stock solution in acetone, nanoparticles were prepared by nano-precipitation or nanoemulsion as in Example 3. As the surfactant concentration (if present in the aqueous solution), a final concentration of 1% for the nanoemulsion and 0.3% for the nano-precipitation was sought.

The nanoparticles were purified differently as described in the Table. Thereafter, all resulting particle suspensions were frozen in the −80° C. freezer and then lyophilized overnight. Approximately 2 mg of the powder was then resuspended in 1 mL ultrapure water and recharacterized. The ratio of the values was calculated by dividing the corresponding readings after lyophilization by those after preparation. A part of the resulting nanoparticles was dissolved in DMF[6)] and the encapsulation efficiency of the active ingredient was determined by means of UV/VIS spectroscopy via its absorption.

TABLE 13

Properties of PLGA[3)]- Nile Red nanoparticles using P(EtOx)$_{61}$ or P(MeOx)$_{57}$
as a surfactant after preparation by nanoemulsion and nanoprecipitation.

| Active substance | Surfactant | Preparation method | Size [d, nm] | PDI |
|---|---|---|---|---|
| Nile Red | P(EtOx)$_{61}$ | Nanoprecipitation | 160.8 ± 1.5 | 0.053 ± 0.028 |
| Nile Red | P(EtOx)$_{61}$ | Nanoemulsion | 190.7 ± 1.9 | 0.124 ± 0.013 |
| Nile Red | P(MeOx)$_{57}$ | Nanoprecipitation | 151.2 ± 0.8 | 0.065 ± 0.021 |
| Nile Red | P(MeOx)$_{57}$ | Nanoemulsion | 180.0 ± 0.8 | 0.099 ± 0.014 |
| Nile Red | None | Nanoprecipitation | 145.2 ± 2.5 | 0.075 ± 0.018 |
| Nile Red | None | Nanoemulsion | n.a. | n.a. | n.a. = not available (not available).

TABLE 14

Properties of PLGA[3)]- Nile Red nanoparticles using P(EtOx)$_{61}$
or P (MeOx)$_{57}$ as surfactant after purification and lyophilization,

| Additive | P(EtOx)$_6$i | | P(MeOx)$_{57}$ | | None | |
|---|---|---|---|---|---|---|
| Purification method | Size [d, nm] | PDI | Size [d, nm] | PDI | Size [d, nm] | PDI |
| After preparation | 160.8 ± 1.5 | 0.053 ± 0.028 | 169.0 ± 2.5 | 0.069 ± 0.021 | 145.2 ± 2.5 | 0.075 ± 0.018 |
| Lyophilization without purification | 168.0 ± 1.6 | 0.087 ± 0.031 | n.a. | n.a. | n.a. | n.a. |
| Centrifugation and resuspension in 1 mL 0.5% POx solution | 184.3 ± 1.6 | 0.145 ± 0.028 | 187.4 ± 3.2 | 0.123 ± 0.052 | n.r. | n.r. |
| Syringe filtration and addition of 1 mL 0.5% POx solution | 167.7 ± 3.2 | 0.148 ± 0.045 | 233.1 ± 8.4 | 0.314 ± 0.022 | 180.5 ± 1.6 | 0.169 ± 0.020 |
| Syringe filtration | 161.7 ± 3.4 | 0.157 ± 0.011 | n.a. | n.a. | n.a. | n.a. | n.a.: not available (not available because the nanoparticles were too strongly aggregated),
n.r.: not resuspendable.

TABLE 15

Relationships of the properties of PLGA[3]- Nile Red nanoparticles using P(EtOx)$_{61}$ or P(MeOx)$_{57}$ as surfactant after purification and lyophilization.

| | P(EtOx)$_{61}$ | | | P(MeOx)$_{57}$ | | | None | | |
|---|---|---|---|---|---|---|---|---|---|
| Additive Purification method | Size ratio | PDI ratio | EE [μg mg$^1$] | Size ratio | PDI ratio | EE [μg mg$^1$] | Size ratio | PDI ratio | EE [μg mg$^1$] |
| Lyophilization without purification | 1.04 | 1.64 | 0.52 | n.a. | n.a. | n.a. | 28.21 | 12.23 | 1.53 |
| Centrifugation and resuspension in 1 mL 0.5% POx solution | 1.14 | 2.74 | 0.28 | 1.15 | 1.71 | 0.32 | n.a. | n.a. | n.a. |
| Syringe filtration and addition of 1 mL 0.5% POx solution | 1.04 | 2.79 | 0.21 | n.a. | n.a. | n.a. | 1.24 | 2.25 | 0.28 |
| Syringe filtration | 1.01 | 2.96 | 0.51 | n.a. | n.a. | n.a. | n.a. | n.a. | n.a. |

[3]) PLGA = lactic acid-glycolic acid copolymer
[6]) DMF = dimethylformamide
EE: Encapsulation efficiency.

EXAMPLE 8

Encapsulation of PKC 412[7]

10 mg PLGA[3] was dissolved in 1 mL acetone. 0.3 mg PKC 412[7] was dissolved in 30 μL DMSO[8] and added to the PLGA[3] solution. Then, the polymer-active substance solution was added by syringe pump at a defined rate with constant stirring into a vessel with 10 mL of an aqueous solution, optionally containing a surfactant. The organic solvent was then evaporated overnight with constant stirring and the nanoparticles were characterized in terms of their particle diameter and PDI. Thereafter, all resulting particle suspensions were frozen in the −80° C. freezer and then lyophilized overnight. Approximately 2 mg of the particles was then resuspended in 1 mL ultrapure water or a 0.5% solution of the corresponding poly(2-oxazoline) and recharacterized.

The ratio of the values was calculated by dividing the corresponding readings after lyophilization by those after preparation. A part of the resulting nanoparticles was dissolved in DMSO[8] and the encapsulation efficiency of the active ingredient was determined by means of UV/VIS spectroscopy via its absorption.

The invention claimed is:

1. A composition comprising a water-soluble poly(oxazoline) compound and organic polymer particles, wherein the organic polymer particles comprise a polyester; a mean diameter D$_{50}$ of the organic polymer particles is less than 10 μm; and the water-soluble poly(oxazoline) compound is not covalently bonded to the polymeric particles.

2. The composition according to claim 1, characterized in that the polyester is a polyhydroxyalkanoate.

3. The composition according to claim 2, characterized in that the polyhydroxyalkanoate is a lactic acid homo- or copolymer.

4. A composition comprising a water-soluble poly(oxazoline) compound and organic polymer particles, wherein a mean diameter D$_{50}$ of the organic polymer particles is less than 10 μm; the organic particles being selected from the group of polyolefins, polyvinylaromatics, polyvinyl esters, polyesters, polyamides, polyimides, polycarboxylic acids, polycarboxylic acid esters, polycarboxylic acid amides, polynitriles, polysulfonic acids, polyketones, polysulfones, polymeric polyols, polyurethanes, proteins, polymeric carbohydrates, nucleic acids or a mixture of two or more of these polymers;

TABLE 16

Properties of PLGA-PKC 412$^{3,7)}$ nanoparticles using P(EtOx)$_{61}$ or P(MeOx)$_{57}$ as surfactant after purification and lyophilization.

| | After preparation | | After lyophilization | | Ratio | | |
|---|---|---|---|---|---|---|---|
| Surfactant | Size [d, nm] | PDI | Size [d, nm] | PDI | Size | PDI | EE [μg mg'] |
| P(EtOx)$_{61}$ | 168.6 ± 2.4 | 0.061 ± 0.019 | 178.9 ± 2.0 | 0.058 ± 0.025 | 1.06 | 0.95 | 0 |
| P(MeOx)$_{57}$ | 184.6 ± 1.1 | 0.063 ± 0.034 | 190.4 ± 2.4 | 0.086 ± 0.022 | 1.03 | 1.36 | 0.92 ± 0.08 |
| None | 156.1 ± 0.9 | 0.077 ± 0.024 | 7272 ± 2494 | 0.740 ± 0.383 | n.a. | n.a. | 0.98 ± 0.31 |

[3]) PLGA = lactic acid-glycolic acid copolymer
[7]) PKC 412 =
[9S-(9α,10β,11β,13α)]-N-(2,3,10,11,12,13-hexahydro-10-methoxy-9-methyl-1-oxo-9,13-epoxy-1H,9H-di-indolo[1,2,3-gh:3',2',1'lm]pyrrolo[3,4-y7[1,7]benzodiazonin-11-yl)-N-methylbenzamide
[8]) DMSO = dimethyl sulfoxide
n.a.: not available (not because the nanoparticles were too strongly aggregated).
EE: Encapsulation efficiency.

the organic polymer particles contain one or more pharmaceutically active substances; and the water-soluble poly(oxazoline) compound is not covalently bonded to the organic polymeric particles.

5. The composition according to 1, wherein the organic polymer particles have diameters in the range of 50 to 999 nm.

6. The composition according to claim 1, wherein the organic polymer particles form a dispersed phase in a hydrophilic liquid.

7. The composition according to claim 4, wherein the organic polymer particles are in solid form and are coated by the poly(oxazoline).

8. The composition according to claim 4, wherein the organic polymer particles have diameters in the range of 50 to 999 nm.

9. The composition according to claim 4, wherein the organic polymer particles form a dispersed phase in a hydrophilic liquid.

10. The composition according to claim 4, wherein the organic polymer particles are in solid form and are coated by the poly(oxazoline).

11. The composition according to claim 4, wherein the organic polymer particles comprise a polyester.

12. The composition of claim 1, wherein at least 90 wt % of the water-soluble poly(oxazoline) compound has a recurring structural unit of formula I: $-NR^1-CR^3H-CR^4H-$ (I), wherein $R^1$ is $-CO-R^2$ with $R^2$ being hydrogen or methyl or ethyl; and $R^3$, $R^4$ are independently hydrogen, methyl, ethyl, propyl, or butyl.

13. The composition of claim 12, wherein at least 95 wt % of the water-soluble poly(oxazoline) compound has the recurring structural unit of formula I.

14. The composition of claim 1, wherein the water-soluble poly(oxazoline) is a homopolymer.

15. The composition of claim 4, wherein at least 90 wt % of the water-soluble poly(oxazoline) compound has a recurring structural unit of formula I: $-NR^1-CR^3H-CR^4H-$ (I), wherein $R^1$ is $-CO-R^2$ with $R^2$ being hydrogen or methyl or ethyl; and $R^3$, $R^4$ are independently hydrogen, methyl, ethyl, propyl, or butyl.

16. The composition of claim 15, wherein at least 95 wt % of the water-soluble poly(oxazoline) compound has the recurring structural unit of formula I.

17. The composition of claim 4, wherein the water-soluble poly(oxazoline) is a homopolymer.

18. The composition of claim 4, further comprising an auxiliary agent and/or an additive.

* * * * *